United States Patent
Chen et al.

(10) Patent No.: US 9,725,773 B2
(45) Date of Patent: Aug. 8, 2017

(54) MOLECULAR MARKERS ASSOCIATED WITH GREEN SNAP IN MAIZE

(71) Applicant: Dow AgroSciences LLC, Indianapolis, IN (US)

(72) Inventors: Wei Chen, Carmel, IN (US); Tiffany King, Fishers, IN (US); Yanxin Star Gao, Waunakee, WI (US); Jafar Mammadov, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/879,294

(22) Filed: Oct. 9, 2015

(65) Prior Publication Data

US 2016/0102370 A1    Apr. 14, 2016

Related U.S. Application Data

(60) Provisional application No. 62/062,506, filed on Oct. 10, 2014.

(51) Int. Cl.
| | | |
|---|---|---|
| C12Q 1/68 | (2006.01) | |
| A01H 1/04 | (2006.01) | |
| A01H 5/10 | (2006.01) | |

(52) U.S. Cl.
CPC ............. *C12Q 1/6895* (2013.01); *A01H 1/04* (2013.01); *A01H 5/10* (2013.01); *C12Q 2600/13* (2013.01); *C12Q 2600/156* (2013.01)

(58) Field of Classification Search
None
See application file for complete search history.

(56) References Cited

PUBLICATIONS

Cordova et al. (CIMMYT Central American/Caribe Regional Maize Program, 1988 Mid Year Progress Report, 1988, pp. 1-30).*

* cited by examiner

*Primary Examiner* — Brent Page
*Assistant Examiner* — Jared Shapiro
(74) *Attorney, Agent, or Firm* — Eric J. Kraus

(57) ABSTRACT

This invention relates to methods for identifying maize plants that having increased green snap tolerance. The methods use molecular markers to identify and to select plants with increased green snap tolerance. Maize plants generated by the methods of the invention are also a feature of the invention.

1 Claim, No Drawings

SEQUENCE LISTING

```
<160> NUMBER OF SEQ ID NOS: 7

<210> SEQ ID NO 1
<211> LENGTH: 101
<212> TYPE: DNA
<213> ORGANISM: Zea mays

<400> SEQUENCE: 1
gaagctgtcg gcgtctccat tgaagtccat gtccatgttc gtctgtcgat rgagccgtac      60
gcccgtacca ctgtacgcag cggaggaaga ggatggcaca a                        101

<210> SEQ ID NO 2
<211> LENGTH: 401
<212> TYPE: DNA
<213> ORGANISM: Zea mays

<400> SEQUENCE: 2
tagtcggtac ccagccagat tcgggctccg gttcacctaa atccgtgttt tcccgtgatg      60
tccaggtgat ttcttcccct ttgatctgct gtgacgtggg agatgccgcc gaagtctaag     120
```

```
aggggtggcg ctgccgccgc gaggaaggcg ccggtgacga ggggccggat ggggagggcg      180
caggctgcgg cggaagcggc kccggttgtg gaggagatgg aggcgcctgc tgaggaggtg      240
aaggccgccg aggaggtccc gaaggtggtg gaggcaccga aggtggtgga ggactcgaag      300
gtggtggagg agccgaaacc ctcgcctctg ctgccgcaac agccggtggt ggtggtggag      360
aaagactccg atatcgcagc caacggtgcc aaccagggtg a                         401

<210> SEQ ID NO 3
<211> LENGTH: 101
<212> TYPE: DNA
<213> ORGANISM: Zea mays

<400> SEQUENCE: 3
tctctgtgag gctgagaccg ctcagcgaca aggagattgc aaggagggac mcggcggagt       60
gggagtgcat caacgacact accatcatct cccggagcac c                         101

<210> SEQ ID NO 4
<211> LENGTH: 101
<212> TYPE: DNA
<213> ORGANISM: Zea mays

<400> SEQUENCE: 4
gcacctttgc agagaagcct taggagcaaa tcggcaagtt ggggattcac rtcgccaggt       60
aattccacag gatcattggc aatctatttt ggagtaacca c                         101

<210> SEQ ID NO 5
<211> LENGTH: 101
<212> TYPE: DNA
<213> ORGANISM: Zea mays

<400> SEQUENCE: 5
tggtaaaatc acgacgtcag ccttatcctc ttctcaccgt gaaatcgcgt ytctctgtcg       60
acgtcgtgca gagtactccc tccctcgcca cagccgccgc c                         101

<210> SEQ ID NO 6
<211> LENGTH: 101
<212> TYPE: DNA
<213> ORGANISM: Zea mays

<400> SEQUENCE: 6
acacgttgta aagattcatt attgagctgg atgcgtgtac ggtaaacatg ytgtgacctg       60
tgaagattca tcatttgagt tgggtgctag tacaattgca g                         101

<210> SEQ ID NO 7
<211> LENGTH: 101
<212> TYPE: DNA
<213> ORGANISM: Zea mays

<400> SEQUENCE: 7
gggttgtgac tagcatcaat caagtctgct cttttgctg catctctggg ytgggtctat        60
cgtttatgca atacaatgct ttttctgatg atgattatat g                         101
```

MOLECULAR MARKERS ASSOCIATED WITH GREEN SNAP IN MAIZE

This application claims a priority based on provisional application 62/062,506 which was filed in the U.S. Patent and Trademark Office on Oct. 10, 2014, the entire disclosure of which is hereby incorporated by reference.

FIELD OF THE INVENTION

The present invention relates to methods useful in selecting for increased green snap tolerance in maize plants.

BACKGROUND OF THE INVENTION

Green snap (GS), also called brittle snap, refers to the stalk breakage at or below the ear node when maize is rapidly growing. GS is environmentally dependent. It is hard to predict the severity of the phenomenon. Abiotic factors that are observed to cause GS include strong winds at the most vulnerable growth stage, excessive nitrogen treatment, high temperature and high soil moisture conditions (Elmore, 1999, 2003; Wilhelm, 1999). However, GS is conditioned not only by environmental factors. The genetics of maize also has a significant contribution. It has been observed that certain lines of maize are more tolerant to GS than others.

Green snap could lead to yield loss up to 90% when high wind passes through the corn fields during the rapid growth (elongation) period of vegetative growth. It is not a rare phenomenon. In July 1993 and 1994, severe storms with wind at 100 mph wiped across the western U.S. corn belt, destroyed many corn fields. Almost every other year, green snap causes significant damages in Nebraska, Iowa, Minnesota, Illinois, and periodically in Ohio. However, GS is unpredictable. It depends on both biotic and abiotic factors. The same variety of corn planted a few days apart could have different levels of GS.

Meanwhile, the yield effects of GS may not be as straightforward as suggested by Roger Elmore and Richard B. Ferguson from the University of Nebraska-Lincoln in a linear fashion (based on data from 1993 and 1994): decrease 1% for every 1% increase in stalk breakage. Studies from the University of Minnesota indicate that the grain production of standing plants might compensate for grain loss from broken plants. Depending on where the breakage occurs, stalks broken below the dominant ear have significantly higher yield loss than above the ear with an average of an additional 16 percent less yield.

Green snap has become an increasing issue for seed industries producing high yielding hybrids. The corn hybrids tend to be tall and grow fast, which make them GS-vulnerable. Ironically, the best farming practice, rotating with soybean, tilling, efficient nitrogen use, high moisture and the use of fungicide with growth regulator make the plants more susceptible to the GS. Although genetics have been an effective way to fight against damages from GS, not many studies underlining the resistance has been published. Corn researchers at Pioneer Hi-Bred International (PHI) have modified a mechanical detasseler to snap corn stalk mimicking the natural GS damage (Barreiro et al, 2011). With its artificial breakage device, PHI has successfully selected high yield hybrids with moderate to high level of GS tolerance. In 1999, Benson presented his QTL analysis in an elite non-stiff stalk breeding population in the 63$^{rd}$ Corn and Sorghum Research Conference. In his study, three QTLs explained 66% of the genetic variation.

SUMMARY OF THE INVENTION

One embodiment of the present invention is a method for selecting a plant displaying altered GS tolerance. The method includes the steps of: a) detecting at least one marker nucleic acid; and, b) selecting a plant comprising the marker nucleic acid, thereby selecting a plant having increased GS tolerance. The plant is preferably a maize plant. The altered GS tolerance is preferably increased GS tolerance.

In embodiments of the invention, the marker nucleic acid is selected from the group consisting of PZE-102041193, chr2_23315995, PZE-102043574, PZE-102043924, PZE-102045178, PZE-102045518, and PZE-102048084.

In embodiments of the invention, at least one marker nucleic acid is selected, preferably, at least two marker nucleic acids are selected, more preferably at least three marker nucleic acids are selected.

In yet another embodiment of the invention is a method for selecting a maize plant having increased GS tolerance, the method comprising: a) detecting at least one marker nucleic acid, wherein at least one marker nucleic acid is selected from the group consisting of PZE-102041193, chr2_23315995, PZE-102043574, PZE-102043924, PZE-102045178, PZE-102045518, and PZE-102048084; and, b) selecting a plant comprising the one marker nucleic acid, thereby selecting a maize plant having increased GS tolerance. Maize plants obtained by the methods described herein are also contemplated by the present invention.

BRIEF DESCRIPTION AND SEQUENCE LISTINGS

The invention can be more fully understood from the following detailed description and the accompanying Sequence Listing, which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

SEQ ID NO: 1 contains the PZE-102041193 SNP and flanking sequence.

SEQ ID NO: 2 contains the chr2_23315995 SNP and flanking sequence.

SEQ ID NO: 3 contains the PZE-102043574 SNP and flanking sequence.

SEQ ID NO: 4 contains the PZE-102043924 SNP and flanking sequence.

SEQ ID NO: 5 contains the PZE-102045178 SNP and flanking sequence.

SEQ ID NO: 6 contains the PZE-102045518 SNP and flanking sequence.

SEQ ID NO: 7 contains the PZE-102048084 SNP and flanking sequence.

DETAILED DESCRIPTION OF THE INVENTION

The present invention provides methods for identifying and selecting maize plants with increased GS tolerance. The following definitions are provided as an aid to understand the invention.

The term "allele" refers to one of two or more different nucleotide sequences that occur at a specific locus.

An "amplicon" is amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

An allele is "associated with" a trait when it is linked to it and when the presence of the allele is an indicator that the desired trait or trait form will occur in a plant comprising the allele.

The "B73 reference genome, version 2" is the physical and genetic framework of the maize B73 genome. It is the result of a sequencing effort utilizing a minimal tiling path of approximately 19,000 mapped BAC clones, and focusing on producing high-quality sequence coverage of all identifiable gene-containing regions of the maize genome. These regions were ordered, oriented, and along with all of the intergenic sequences, anchored to the extant physical and genetic maps of the maize genome. It can be accessed using a genome browser, the Maize Genome Browser, which is publicly available on the internet and facilitates user interaction with sequence and map data.

A "bacterial artificial chromosome (BAC)" is a cloning vector derived from the naturally occurring F factor of *Escherichia coli*. BACs can accept large inserts of DNA sequence. In maize, a number of BACs, or bacterial artificial chromosomes, each containing a large insert of maize genomic DNA, have been assembled into contigs (overlapping contiguous genetic fragments, or "contiguous DNA").

"Backcrossing" refers to the process whereby hybrid progeny are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires Les Colloques, Vol. 72, pp. 45-56, and Openshaw et al., (1994) Marker-assisted Selection in Backcross Breeding, Analysis of Molecular Marker Data, pp. 41-43. The initial cross gives rise to the F1 generation; the term "BC1" then refers to the second use of the recurrent parent; "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

The term "complement" refers to a nucleotide sequence that is complementary to a given nucleotide sequence, i.e., the sequences are related by the base-pairing rules.

The term "contiguous DNA" refers to overlapping contiguous genetic fragments.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, an "elite line" is any line that has resulted from breeding and selection for superior agronomic performance.

A "favorable allele" is the allele at a particular locus that confers, or contributes to, a desirable phenotype, e.g., increased GS tolerance, or alternatively, is an allele that allows the identification of plants with decreased GS tolerance that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or chromosomes) within a given species, generally depicted in a diagrammatic or tabular form. For each genetic map, distances between loci are measured by the recombination frequencies between them, and recombinations between loci can be detected using a variety of molecular genetic markers (also called molecular markers). A genetic map is a product of the mapping population, types of markers used, and the polymorphic potential of each marker between different populations. The order and genetic distances between loci can differ from one genetic map to another. However, information such as marker position and order can be correlated between maps by determining the physical location of the markers on the chromosome of interest, using the B73 reference genome, version 2, which is publicly available on the internet. One of ordinary skill in the art can use the publicly available genome browser to determine the physical location of markers on a chromosome.

The term "Genetic Marker" shall refer to any type of nucleic acid based marker, including but not limited to, Restriction Fragment Length Polymorphism (RFLP) (Botstein et al, 1998), Simple Sequence Repeat (SSR) (Jacob et al., 1991), Random Amplified Polymorphic DNA (RAPD) (Welsh et al., 1990), Cleaved Amplified Polymorphic Sequences (CAPS) (Rafalski and Tingey, 1993, Trends in Genetics 9:275-280), Amplified Fragment Length Polymorphism (AFLP) (Vos et al, 1995, Nucleic Acids Res. 23:4407-4414), Single Nucleotide Polymorphism (SNP) (Brookes, 1999, Gene 234:177-186), Sequence Characterized Amplified Region (SCAR) (Pecan and Michelmore, 1993, Theor. Appl. Genet, 85:985-993), Sequence Tagged Site (STS) (Onozaki et al. 2004, Euphytica 138:255-262), Single Stranded Conformation Polymorphism (SSCP) (Orita et al., 1989, Proc Natl Aced Sci USA 86:2766-2770). Inter-Simple Sequence Repeat (ISR) (Blair et al. 1999, Theor. Appl. Genet. 98:780-792), Inter-Retrotransposon Amplified Polymorphism (IRAP), Retrotransposon-Microsatellite Amplified Polymorphism (REMAP) (Kalendar et al., 1999, Theor. Appl. Genet 98:704-711), an RNA cleavage product (such as a Lynx tag), and the like.

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple led, or, more generally, the term genotype can be used to refer to an individual's genetic make-up for all the genes in its genome.

"Genotype by environment interaction" (GxE) refers to the phenotypic effect of interactions between genes and the environment. GxE interaction is exploited by plant and animal breeders to benefit agriculture. For example, plants can be bred to have tolerance for specific environments, such as high or low water availability.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

"Green Snap (GS)" is a term which describes a corn plant stalk which has been broken by high winds. GS typically occurs at or below the ear, but can occur at any position along the stalk. GS can occur at various developmental stages, but most often occurs between the vegetative stages of V5 and V8 and between the vegetative V12 stage and the reproductive R1 stage.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to sequence, polymorphisms at a particular locus, such as a single marker locus, or sequence polymorphisms at multiple loci along a chromosomal segment in a given genome. The former can also be referred to as "marker haplotypes" or "marker alleles", while the latter can be referred to as "long-range haplotypes".

The "heritability ($h^2$)" of a trait within a population is the proportion of observable differences in a trait between individuals within a population that is due to genetic differences. The $h^2$ value of the QTL is a percentage of variation that is explained by genetics, instead of environment.

A "heterotic group" comprises a set of genotypes that perform well when crossed with genotypes from a different heterotic group (Hallauer at al. (1998) Corn breeding, p. 463-564. In G. F. Sprague and J. W. Dudley (ed) Corn and corn improvement). Inbred lines are classified into heterotic groups, and are further subdivided into families within a heterotic group, based on several criteria such as pedigree, molecular marker-based associations, and performance in hybrid combinations (Smith at al. (1990) Theor. Appl. Gen. 80:833-840). The two most widely used heterotic groups in the United States are referred to as "Iowa Stiff Stalk Synthetic" (BSSS) and "Lancaster" or "Lancaster Sure Crop" (sometimes referred to as NSS, or Iron-Stiff Stalk).

The term "heterozygous" means a genetic condition wherein different alleles reside at corresponding loci on homologous chromosomes.

The term "homozygous" means a genetic condition wherein identical alleles reside at corresponding loci on homologous chromosomes.

The term "hybrid" means a progeny of mating between at least two genetically dissimilar parents. Without limitation, examples of mating schemes include single crosses, modified single cross, double modified single cross, three-way cross, modified three-way cross, and double cross wherein at least one parent in a modified cross is the progeny of a cross between sister lines.

"Hybridization" or "nucleic acid hybridization" refers to the pairing of complementary RNA and DNA strands as well as the pairing of complementary DNA single strands.

The term "hybridize" means the formation of base pairs between complementary regions of nucleic acid strands.

The term "inbred" means a line that has been bred for genetic homogeneity.

The term "indel" refers to an insertion or deletion, wherein one line may be referred to as having an insertion relative to a second line, or the second line may be referred to as having a deletion relative to the first line.

The term "introgression" or "introgressing" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background. For example, the GS locus described herein may be introgressed into a recurrent parent that has increased GS tolerance. The recurrent parent line with the introgressed gene or locus then has increased GS tolerance.

As used herein, the term "linkage" is used to describe the degree with which one marker locus is associated with another marker locus or some other locus (for example, a GS locus). The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units for cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10 (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits for both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same chromosome.) As used herein, linkage can be between two markers, or alternatively between a marker and a phenotype. A marker locus can be "associated with" (linked to) a trait, e.g., decreased green snap. The degree of linkage of a molecular marker to a phenotypic trait is measured, e.g. as a statistical probability of co-segregation of that molecular marker with the phenotype.

Linkage disequilibrium is most commonly assessed using the measure $r^2$, which is calculated using the formula described by Hill, W. G. and Robertson, A, Theor Appl. Genet 38:226-231 (1988). When $r^2=1$, complete LD exists between the two marker loci, meaning that the markers have not been separated by recombination and have the same allele frequency. Values for $r^2$ above $\frac{1}{3}$ indicate sufficiently strong LD to be useful for mapping (Ardlie at al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome where a gene or marker is located.

"Maize" refers to a plant of the *Zea mays* L. ssp. *mays* and is also known as "corn".

The term "maize plant" includes: whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

A "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g. SSRs, RFLPs, AFLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of maize molecular markers are known in the art, and are published or available from various sources, such as the Maize GDB Internet resource and the Arizona Genomics Institute Internet resource run by the University of Arizona.

Markers corresponding to genetic polymorphisms between members of a population can be detected by methods well-established in the art. These include, e.g., DNA sequencing, PCR-based sequence specific amplification methods, detection of FLPs, detection of isozyme markers, detection of polynucleotide polymorphisms by allele specific hybridization (ASH), detection of amplified variable sequences of the plant genome, detection of self-sustained sequence replication, detection of SSRs, detection of SNPs, or detection of FLPs. Well established methods are also known for the detection of expressed sequence tags (ESTs) and SSR markers derived from EST sequences and RAPDs.

A "marker allele", alternatively an "allele of a marker locus", can refer to one of a plurality of polymorphic nucleotide sequences found at a marker locus in a population that is polymorphic for the marker locus.

"Marker assisted selection" (or MAS) is a process by which phenotypes are selected based on marker genotypes.

"Marker assisted counter-selection" is a process by which marker genotypes are used to identify plants that will not be selected, allowing them to be removed from a breeding program or planting.

A "marker locus" is a specific chromosome location in the genome of a species when a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

A "marker probe" is a nucleic add sequence or molecule that can be used to identify the presence of a marker locus, e.g., a nucleic acid probe that is complementary to a marker locus sequence, through nucleic add hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e. genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a via a plant without the insertion. Thus, the marker need only indicate whether the indel region is present or absent. Any suitable marker detection technology may be used to identify such a hybridization marker, e.g., SNP technology is used in the examples provided herein.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate. "G" for guanylate or deoxyguanylate. "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "phenotype", or "phenotypic trait" or "trait" refers to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA that is too common to be due merely to new mutation. A polymorphism must have a frequency of at least 1% in a population. A polymorphism can be a single nucleotide polymorphism, or SNP, or an insertion/deletion polymorphism, also referred to herein as an "indel".

The term "progeny" refers to the offspring generated from a cross.

A "progeny plant" is generated from a cross between two plants.

A "reference sequence" is a defined sequence used as a basis for sequence comparison. The reference sequence is obtained by genotyping a number of lines at the locus, aligning the nucleotide sequences in a sequence alignment program (e.g. Sequencher), and then obtaining the consensus sequence of the alignment.

A "single nucleotide polymorphism (SNP)" is an allelic single nucleotide-A, T, C or G-variation within a DNA sequence representing one locus of at least two individuals of the same species. For example, two sequenced DNA fragments representing the same locus from at least two individuals of the same species, AAGCCTA to AAGCTTA, contain a difference in a single nucleotide.

The term "quantitative trait locus (QTL)" means a locus that controls to some degree numerically representable traits that are usually continuously distributed.

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Genetic Mapping

It has been recognized for quite some time that specific genetic loci correlating with particular phenotypes, such as reduced GS, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a trait of interest, such as increased GS tolerance. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) population-based association analysis and 2) traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each, marker locus for each line in the subpopulation. A significant marker-trait association indicates the dose proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, Genetics 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Markers Associated with Green Snap

Markers associated with increased GS tolerance are identified herein. The methods involve detecting the presence of at least one marker allele associated with increased GS tolerance in the germplasm of a maize plant. The marker loci can be selected from the group consisting of PZE-102041193, chr2_23315995, PZE-102043574, PZE-102043924, PZE-102045178, PZE-102045518, and PZE-102048084, and any other marker linked to these markers (linked markers can be determined from the Maize GDB and Panzea resources).

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

Other markers linked to the markers listed in Table 1 can be used to predict GS tolerance in a maize plant. This includes any marker within 50 cM of markers from the group consisting of PZE-102041193, chr2_23315995, PZE-102043574, PZE-102043924, PZE-102045178, PZE-102045518, and PZE-102048084, the markers associated with GS. The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8% 7%, 6%, 5%, 4%, 3%, 2% 1%, 0.75%, 0.5%, 0.25.degree., or less) are said to be "proximal to" each other.

Although particular marker alleles can show co-segregation with increased GS tolerance, it is important to note that the marker locus is not necessarily responsible for the expression of the increased GS tolerance phenotype. For example, it is not a requirement that the marker polynucleotide sequence be part of a gene that imparts increased GS tolerance (for example, be part of the gene open reading frame). The association between a specific marker allele and the increased GS tolerance phenotype is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the donor parent used to create segregating populations. This does not change the fact that the marker can be used to monitor segregation of the phenotype. It only changes which marker allele is considered favorable in a given segregating population.

The present invention includes isolated nucleic acid molecules. Such molecules include those nucleic acid molecules capable of detecting a polymorphism genetically or physically linked to a GS locus. Such molecules can be referred to as markers.

Additional markers can be obtained that are linked to the GS locus by available techniques. In one aspect, the nucleic acid molecule is capable of detecting the presence or absence of a marker located less than 30, 20, 10, 5, 2, or 1 cM from the GS locus. In another aspect, the nucleic acid molecule is capable of detecting a marker in a locus selected from the group consisting of PZE-102041193, chr2_23315995, PZE-102043574, PZE-102043924, PZE-102045178, PZE-102045518, and PZE-102048084. In a further aspect, a nucleic acid molecule is selected from the group consisting of SEQ ID NO: 1 through SEQ ID NO: 7 fragments thereof, complements thereof, and nucleic acid molecules capable of specifically hybridizing to one or more of these nucleic acid molecules.

A marker of the invention can also be a combination of alleles at marker loci, otherwise known as a haplotype. The skilled artisan would expect that there might be additional polymorphic sites at marker loci in and around the GS markers identified herein, wherein one, or more polymorphic sites is in linkage disequilibrium (LD) with an allele associated with increased GS tolerance. Two particular alleles at different polymorphic sites are said to be in LD if the presence of the allele at one of the sites tends to predict the presence of the allele at the other site on the same chromosome (Stevens, Mol. Diag. 4:309-17 (1999)).

Marker Assisted Selection

Molecular markers can be used in a variety of, plant breeding applications (e.g. see Staub et al. (1996) Hortscience 729-741; Tanksley (1983) Plant Molecular Biology Reporter 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true with traits that are difficult to phenotype due to their dependence on environmental conditions. This category includes traits related to the resistance to biotic and abiotic stresses. This category also includes traits that are very expensive to phenotype because of laborious artificial inoculation or maintenance of managed stress environments. Another category of traits includes those which are associated with destruction of plant per se. Destructive phenotyping has been a bottleneck to implement MAS for the seed quality traits. Because DNA marker assays are not environmentally dependent, are robust, reliable, less laborious, less costly and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). Crop Sci; 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al. (1998) Genetics 120:579-585). In classical breeding it is usually only by chance that recombinations are selected that contribute to a reduction in the size of the donor segment (Tanksley et al. (1989). Biotechnology 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will avow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with, markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of the B73 reference genome, version 2 and the integrated linkage maps of the maize genome containing increasing densities of public maize markers, has facilitated maize genetic mapping and MAS. See, e.g. the IBM2 Neighbors maps, which are available online on the Maize GDB website.

The key components to the implementation of MAS are (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) Nucleic Acid Research 17: 6463-6471; Wang et al. (1994) Theoretical and Applied Genetics, 88:1-6). Polymorphisms arise due to variation in the number of repeat units, probably caused by slippage during DNA replication (Levinson and Gutman (1987) Mol Biol Evol 4: 203-221). The variation in repeat length may be detected by designing PCR primers to the conserved non-repetitive flanking regions (Weber and May (1989) Am J Hum Genet. 44:388-396), SSRs are highly suited to mapping and MAS as they are multi-allelic, codominant, reproducible and amenable to high throughput automation (Rafalski et al. (1996) Generating and using DNA markers in plants. In Non-mammalian genomic analysis: a practical guide. Academic Press, pp 75-135).

Various types of SSR markers can be generated, and SSR profiles from resistant lines can be obtained by gel electrophoresis of the amplification products. Scoring of marker genotype is based on the size of the amplified fragment. An SSR service for maize is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). Plant Mol Biol 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 Plant Molecular Biology 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) Hum Mutat 17 pp, 475-492: Shi (2001) Clin Chem 47, pp. 164-172; Kwok (2000) Pharmacogenomics 1, pp. 95-100: Bhattramakki and Rafalski (2001) Discovery and application of single nucleotide polymorphism markers in plants. In: R, J Henry, Ed, Plant Genotyping: The DNA Fingerprinting of Plants, CABI Publishing, VVallingford. A wide range of commercially available technologies utilize these and other methods to interrogate SNPs including Masscode™. (Qiagen), Invader® (Third Wave Technologies), SnapShot® (Applied Biosystems), Taqman® (Applied Biosystems) and Beadarrays™ (Illumina).

A number of SNPs together within a sequence, or across linked sequences, can be used to describe a haplotype for any particular genotype (Ching et al. (2002), BMC Genet. 3:19 pp Gupta et al. 2001, Rafalski (2002b), Plant Science 162:329-333). Haplotypes can be more informative than, single SNPs and can be more descriptive of any particular genotype. For example, single SNP may be allele 'T' for a specific line or variety with increased GS tolerance, but the allele 'T' might also occur in the maize breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

The sequences listed in Table 1 can be readily used to obtain additional polymorphic SNPs (and other markers) linked to the markers listed in this disclosure that are associated with a GS QTL. Markers listed in Table 1 can be hybridized to BACs or other genomic libraries, or electronically aligned with genome sequences, to find new sequences in the same approximate location as the described markers.

In addition to SSRs, FLPs and SNPs, as described above, other types of molecular markers are also widely used, including but not limited to, markers derived from EST sequences, RAPDs, and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) Plant Molecular Biology Reporter 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species whose genomes share some level of colinearity at macro- and micro-level with maize, such as rice and sorghum.

In general, MAS uses polymorphic markers that have been identified as having a significant likelihood of co-segregation with increased GS tolerance. Such markers are presumed to map near quantitative trait loci (QTL), give the plant its increased GS tolerance phenotype, and are considered indicators, or markers, for the desired trait. Markers test maize plants for the presence of a desired allele, and those which contain a desired genotype at one or more loci are expected to transfer the desired genotype, along with a desired phenotype, to their progeny. The means to identify maize plants that have increased GS tolerance by identifying plants that have a specified allele from the group consisting of PZE-102041193, chr2_23315995, PZE-102043574, PZE-102043924, PZE-102045178, PZE-102045518, and PZE-102048084, are presented herein.

The marker nucleic acid group presented herein finds use in MAS to select plants that demonstrate increased GS tolerance. Any marker that listed in Table 1 can be used for this purpose. In addition, haplotypes comprising alleles at one or more marker loci from the group consisting of PZE-102041193, chr2_23315995, PZE-102043574, PZE-102043924, PZE-102045178, PZE-102045518, and PZE-102048084 can be used to introduce an increased GS tolerance trait into maize lines or varieties. Any allele or haplotype that is in linkage disequilibrium with an allele associated with increased GS tolerance can be used in MAS to select plants with increased GS tolerance.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1

Marker Framework and Use for Marker Assisted Selection

A set of common markers can be used to establish a framework for identifying markers linked to a QTL. Closely linked markers flanking the locus of interest that have alleles in linkage disequilibrium with a favorable allele at that locus may be effectively used to select for progeny plants with increased GS tolerance. Thus, the markers described in herein, such as those listed in Table 1, as well as other markers genetically or physically mapped to the same chromosomal segment, may be used to select for maize plants with increased GS tolerance. Typically, a set of these markers will be used (e.g. 2 or more, 3 or more, 4 or more, 5 or more) in the regions flanking the locus of interest. Optionally, a marker within the actual gene and/or locus may be used.

TABLE 1

Summary of SNP markers associated with increased green snap tolerance.

| Marker | Seq ID NO | SNP | Donor Allele |
|---|---|---|---|
| PZE-102041193 | 1 | A/G | G |
| chr2_23315995 | 2 | T/G | T |
| PZE-102043574 | 3 | A/C | A |
| PZE-102043924 | 4 | A/G | A |
| PZE-102045178 | 5 | T/C | T |
| PZE-102045518 | 6 | T/C | T |
| PZE-102048084 | 7 | T/C | T |

Example 2

Population for Identification of SNP Markers Associated with Increased Green Snap Tolerance Seventy-five double haploid (DH) lines of a population developed from a cross between 'STC13'×'BE4207' were planted (10-12 kernels/line per row) in two environments, Davenport, Iowa and Mount Vernon, Ind. in 2011. STC13 is an adapted Argentinean inbred line and tolerant to GS. BE4207 is a Dow AgroSciences (DAS) high impact inbred line with an excellent general combining ability. However, BE4207 is highly susceptible to GS. Leaf punches were collected in July 2011, from Sidney and extracted with a standard MagAttract 96 DNA Plant Core Kit (Qiagen, Valencia, Calif.) with a customized BioCel robot system from Agilent Technologies (Santa Clara, Calif.). Prior to PCR, DNA samples were quantified with Quant-iT™ PicoGreen® Quantification Kit (Invitrogen, Carlsbad, Calif.) using manufacturer's instructions.

Example 3

Phenotype Data Collection

Phenotypic data were collected from two locations: Davenport and Mount Vernon in August 2011. Each line had 10 to 12 plants in a row. Phenotype was based on naturally occurred snapping. The GS severity rating was taken from the entire row and the GS phenotype was represented as a ratio of snapped plants to the total number of plants per row. For example, if three plants were snapped out of 12 in total, then GS severity would be 3/12.

As the phenotypic data collected from Davenport and Mount Vernon were based on the naturally occurred stalk breakage, at both locations, there were many lines with no GS, which were either GS tolerant lines or false positive escapes. Since GS is highly environmentally dependant, escape is hard to avoid when the occurrence is from natural wind damage. However, using restricted maximum likelihood (REML) estimation of variance in JMP 9.0 (SAS, Cary, N.C.) revealed a low environment effect with 14.74%. The heritability is moderate: 38.66%, and genotype by environment effect is high, explaining 46.60% of the variation. This is in agreement with the study by Benson (1999), where QTLs accounted for 26% of the total variation.

Example 4

Genotypic Data Collection

SNP genotyping for each DNA sample (200 ng/sample) was performed using DAS custom Infinium iSelect (Illumina, San Diego, Calif.), using the manufacturer's recommended protocol. SNP genotyping data from the Infinium iSelect were analyzed with GenomeStudio 2011.1 software (Illumina, San Diego, Calif.) and a total of 13,972 polymorphic SNPs were identified.

Example 5

Introgression of Increased Green Snap Tolerance into a Corn Plant

Corn breeders can use the SNP markers provided in the present invention to introgress increased GS tolerance into a corn plant. The markers provided in Table 1 can be used to monitor the introgression of the GS QTL into a corn plant.

The introgression of the GS locus is achieved via one or more cycles of backcrossing to a recurrent parent with one or more preferred agronomic characteristics, accompanied by selection to retain the GS locus from the donor parent using the markers of the present invention. Introgression can be monitored by genotyping one or more plants and determining the allelic state of the GS locus. This backcross procedure is implemented at any stage in variety development and occurs in conjunction with breeding for one or more traits of interest including transgenic and nontransgenic traits.

Alternatively, a forward breeding approach is employed wherein the GS locus can be monitored for successful introgression following a cross with a susceptible parent with subsequent generations genotyped for the GS locus and for one or more additional traits of interest, including transgenic and nontransgenic traits.

---

We claim:

1. A method for production of a maize plant having increased green snap tolerance, the method comprising:
   a) isolating nucleic acids from a maize plant;
   b) analyzing the isolated nucleic acids for the presence of a haplotype associated with increased green snap tolerance, wherein the haplotype comprises (a) a "G" at PZE-102041193.51; (b) a "T" at chr2_23315995.201; (c) an "A" at PZE-102043574.51; (d) an "A" at PZE-102043924.51; (e) a "T" at PZE-102045178.51; (f) a "T" at PZE-102045518.51; and, (g) a "T" at PZE-102048084.51;

c) selecting a maize plant having the haplotype;
d) crossing the maize plant having the haplotype with a second maize plant;
e) obtaining progeny seeds from the cross; and,
f) growing at least one maize plant from the progeny seeds, wherein the maize plant grown from the seeds comprises the haploytpe and has increased green snap tolerance when compared with a maize plant that lacks the haplotype.

\* \* \* \* \*